United States Patent [19]

Arnold

[11] Patent Number: 5,386,046

[45] Date of Patent: Jan. 31, 1995

[54] METHOD FOR THE PREPARATION OF PURE CARBOXYETHYL GERMANIUM SESQUIOXIDE

[75] Inventor: Michael J. Arnold, Irvine, Calif.

[73] Assignee: Viva America Marketing, Inc., Costa Mesa, Calif.

[21] Appl. No.: 204,548

[22] Filed: Mar. 2, 1994

[51] Int. Cl.$^6$ .................................................. C07F 7/30
[52] U.S. Cl. ......................................... 556/89; 556/87; 556/105
[58] Field of Search ............................ 556/87, 105, 89

[56] References Cited

U.S. PATENT DOCUMENTS

| | | | |
|---|---|---|---|
| 3,793,455 | 2/1974 | Asai et al. | 424/287 |
| 4,066,678 | 1/1978 | Sato et al. | 260/429 R |
| 4,473,581 | 9/1984 | Ishida et al. | 424/287 |
| 4,898,882 | 2/1990 | Nagahama et al. | 514/492 |
| 4,956,272 | 9/1990 | Kakimoto et al. | 435/1 |
| 4,973,553 | 10/1990 | Miyao et al. | 435/206 |

FOREIGN PATENT DOCUMENTS 2222404  3/1990  United Kingdom .

Primary Examiner—José G. Dees
Assistant Examiner—Porfirio Nazario-Gonzalez
Attorney, Agent, or Firm—Lawrence S. Cohen

[57] ABSTRACT

A synthetic method for generating pure carboxyethyl germanium sesquioxide in the absence of toxic impurities. In the method germanium dioxide and metallic germanium are not used as starting materials. The method involves the production of pure crystals of trichlorogermane propionic acid which are converted to carboxyethyl germanium sesquioxide. The product has an $LD_{50}$ value of at least 5 g/kg.

8 Claims, No Drawings

METHOD FOR THE PREPARATION OF PURE CARBOXYETHYL GERMANIUM SESQUIOXIDE

BACKGROUND

1. Field of the Invention

The present invention relates to a synthetic method for generating pure carboxyethyl germanium sesquioxide, and in particular to a chemical method for synthesizing carboxyethyl germanium sesquioxide that yields the carboxyethyl germanium sesquioxide without trace amounts of germanium dioxide or metallic germanium.

2. Description of the Prior Art

Carboxyethyl germanium sesquioxide (organic germanium) has been shown to have chemotherapeutic value. Nakao Ishida, et. al., U.S. Pat. No. 4,473,581 teach that carboxyethyl germanium sesquioxide can induce interferon production in humans. Nagahama teaches in U.S. Pat. No. 4,898,882 that carboxyethyl germanium sesquioxide can provide the human body resistance against the common cold. Asai in U.S. Pat. No. 3,793,455 describes the use of carboxyethyl germanium sesquioxide as an agent for treatment of hypertension. Although carboxyethyl germanium sesquioxide is a well known compound, its molecular structure has been shown to be dependent on the synthetic method employed.

For use as a chemotherapeutic agent, or as a food supplement, it is required that carboxyethyl germanium sesquioxide be pure, free of unwanted and potentially lethal contaminants germanium dioxide and metallic germanium. Many known methods for synthesizing carboxyethyl germanium sesquioxide provide for the production of germanium sesquioxide contaminated with trace amounts of metallic germanium, or germanium dioxide, since these are used as the starting materials. Trichlorogermanium acrylate moieties (trichlorogermanium acroyl chlorides, trichlorogermanium acrylic acids, trichlorogermanium acroleins and trichlorogermanium alkyl acrylates) are the key intermediates common to such known synthetic routes. Entries described by the prior art to the trichlorogermanium acrylate intermediates, utilize methods that require either oxidation of metallic germanium with hydrochloric acid, or reduction of germanium dioxide and, hence, the probability of the presence of trace amounts of unreacted starting material (metallic germanium or germanium dioxide) in the product is significant.

The present invention does not start with either metallic germanium or germanium dioxide, but rather starts with germanium tetrachloride.

SUMMARY OF THE INVENTION

Accordingly, a major object of the present invention is the provision of a synthetic method that is devoid of the aforementioned drawbacks which to date have characterized this art.

It is the primary object of the present invention to provide a method whereby carboxyethyl germanium sesquioxide can be prepared without contamination from metallic germanium or germanium dioxide.

It is another object of the present invention to provide a method for the production of a carboxyethyl germanium sesquioxide molecular species that is completely non toxic to the human body.

It is another object of the present to provide a method for the production of a carboxyethyl germanium sesquioxide molecular species that has an $LD_{50}$ value of at least 5 g/Kg.

The present method involves the isolation and purification of the intermediate trichlorogermane propionic acid (hereafter referred to as TPA). In this method reaction of germanium tetrachloride in the presence of acrylic acid takes place under ambient conditions to form a mixture of polymeric material and TPA. This mixture is then depolymerized with concentrated hydrochloric acid to form a crude TPA reaction product, which is then recrystallized to a pure TPA form. The pure TPA is then hydrolyzed to form carboxyethyl germanium sesquioxide.

DETAILED DESCRIPTION OF THE INVENTION

The method of the invention involves the steps of forming from the starting material of germanium tetracholoride, an intermediate material, trichlorogermane propionic acid, isolating and purifying the trichlorogermane propionic acid and converting the TPA by hydrolysis to carboxyethyl germanium sesquioxide.

The specific steps of the process are described as follows:

a first mixture is obtained by reacting germanium tetrachloride with tetramethyl disiloxane and acrylic acid. This first mixture consists essentially of trichlorogermane propionic acid (TPA), a polymer and volatile by-products. The reaction profile is:

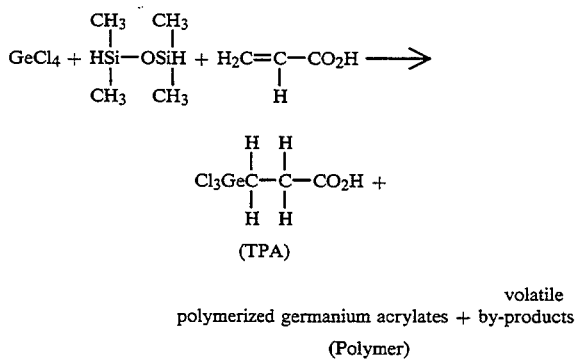

volatile
polymerized germanium acrylates + by-products
(Polymer)

The first mixture is subjected to vacuum distillation to remove the volatiles. This results in a second mixture which consists essentially of TPA plus the polymerized germanium acrylates (hereafter referred to as "polymer"). The chemical profile of this steps is:

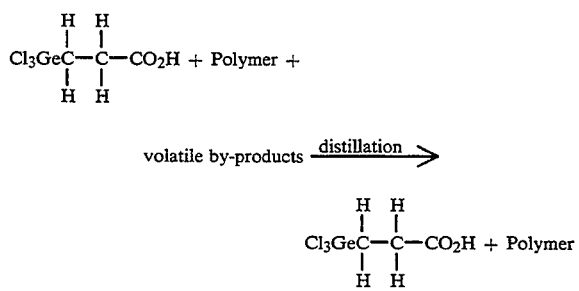

The second mixture is reacted with hydrochloric acid in sufficient amount, preferably in excess, to completely react with the polymer for depolymization, that is to convert the polymer to TPA providing a third mixture consisting essentially of TPA and hydrochloric acid.

The reaction essentially of TPA and hydrochloric acid. The reaction profile is:

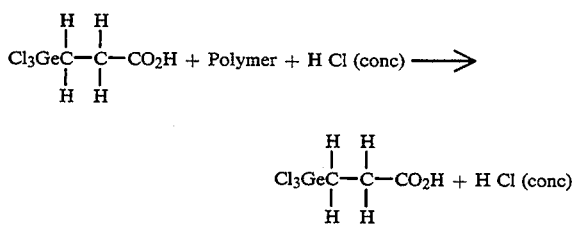

The third mixture is subjected to solvent extraction to separate the hydrochloric acid from the TPA and provide a fourth mixture consisting essentially of TPA and extraction solvent. The preferred solvent is a sufficient amount, preferably in excess, of a halogenated solvent, specifically dichloromethane being most preferred. Chloroform and carbotetrachloride might also work. The reaction profile is:

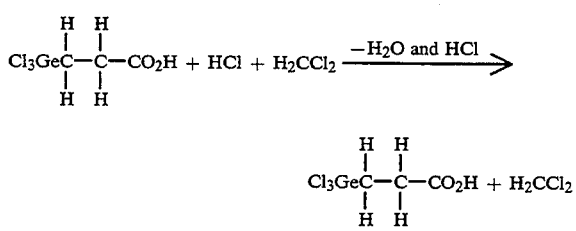

The fourth mixture is subjected to vacuum distillation to remove the solvent ($H_2CCl_2$) resulting in a crude reaction product, consisting essentially of TPA. That is, the TPA is in a form .or mixture presumed to be insufficiently pure. The reaction profile is:

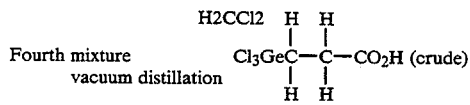

Next the crude TPA reaction product is purified and converted to carboxyethyl germanium sesquioxide by the following steps:

The crude TPA reaction product is dissolved in a minimal amount of boiling non-polar alkyl solvent, preferably hexane, to form upon cooling, high purity crystals of TPA. The hexane is removed and the resulting crystals are washed successively with hexane in order to yield fine pure crystals of TPA. The reaction profile is:

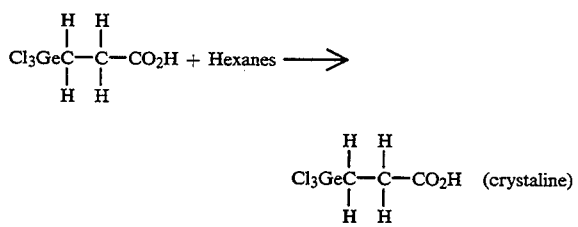

This results in pure crystals of TPA.

Next the pure TPA crystals are reacted in a sufficient amount, preferably in excess, of ammonium hydroxide, to form a fifth mixture consisting of hydrolyzed TPA. Slow addition of concentrated sulfuric acid yields carboxyethyl germanium sesquioxide. The chemical profile is:

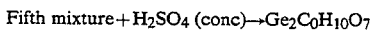

Fifth mixture + $H_2SO_4$ (conc) → $Ge_2C_9H_{10}O_7$

A one-pot synthesis of analytically pure organic germanium is described below.

To a 2 L round bottom flask purged with argon was added successively: germanium tetrachloride (200 g [0.9346 mol]), tetramethyldisiloxane (125 g [0.93 mol]), and acrylic acid (70.0 g [0.97 mol]). The reaction flask was purged with argon then sealed by placement of a ground glass stopper with a teflon sleeve and secured via teflon tape. The slightly cloudy mixture changed to a clear, colorless homogeneous solution within about 2 hours, and this was stirred for seven days at ambient temperature. The volatile components were removed via vacuum (0.5 to 5 mmHg) while the product mixture was heated to an internal temperature of 70° C.-80° C., where it was a homogeneous, clear and colorless viscous solution (melt). Evacuation was continued until no more distillate was observed (ca. 2 hours). This was cooled to an ambient temperature to yield a white amorphous solid. To this was added 950 mL of concentrated HCl. The resulting heterogeneous mixture was warmed to an internal temperature of 60° C.-70° C., and stirred for four hours. The cooled mixture was extracted 3 times with 500 mL of dichloromethane. The combined extracts were evaporated under reduced pressure via rotoryevaporator to give a white amorphous solid. This was dissolved in ca. 1 L boiling hexane (until a clear colorless homogeneous hot solution was obtained), and let cool gently to ambient temperature. The product, trichlorogermanepropionic acid, was isolated via suction filtration, washed once with hexane to give fine prisms, mp 75° C.-79° C. This was immediately taken up (vigorous reaction), with careful addition of 850 mL of ammonium hydroxide (29% ammonia). The resulting turbid mixture was stirred for 4 days at ambient temperature (the mixture changes to a clear, colorless homogeneous solution within 3 hours). To this homogeneous solution was added dropwise over two hours through a reflux condenser 400 mL of concentrated sulfuric acid. NOTE: This is a very vigorous reaction and should be handled with extreme care. A white precipitate formed after addition of ca. 375 mL of acid. The pot was stirred for 48 hours, and then the while solid was isolated via suction filtration, washed successively with 2×150 mL water, 1×150 mL acetone, and 1×200 mL of diethyl ether, then this brilliant white solid was air dried overnight, and then taken up with 150 mL hot water, then cooled and filtered to yield 78.84 g (50%) of analytically pure carboxyethyl germanium sesquioxide.

Although particular embodiments of the invention have been described and illustrated herein, it is recognized that modifications and variations may readily occur to those skilled in the art, and consequently it is intended that the claims be interpreted to cover such modifications and equivalents.

I claim:

1. A method of preparing organic germanium in the absence of any toxic level of germanium dioxide or metallic germanium comprising;
preparing trichlorogermane propionic acid as a crude reaction product from germanium tetrachloride;
forming high purity crystals of trichlorogermane propionic acid from the said crude reaction product of trichlorogermane propionic acid by a crystallization process;

forming a germanium acrylate moiety as a reaction product from hydrolysis of the high purity crystals of trichlorogermane propionic acid;

forming carboxyethyl germanium sesquioxide as a reaction product from acidification of the germanium acrylate moiety.

2. A method of preparing organic germanium in the absence of any toxic level of germanium dioxide or metallic germanium comprising;

reacting germanium tetrachloride, acrylic acid and tetramethly disiloxane to obtain first reaction products in a first mixture;

removing volatiles from the first mixture to obtain a second mixture;

reacting the second mixture with at least an effective amount of hydrochloric acid to obtain a third mixture consisting essentially of trichlorogermane propionic acid and hydrochloric acid;

separating by extraction with an organic solvent trichlorogermane propionic acid from hydrochloric acid in the third mixture to form a fourth mixture;

removing the extraction solvent from the fourth mixture to form a crude reaction product of trichlorogermane propionic acid;

dissolving the crude reaction product with a non-polar alkyl solvent to form high purity crystals of trichlorogermane propionic acid;

hydrolyzing the high purity crystals of trichlorogermane propionic acid in ammonium hydroxide to form a fifth mixture;

reacting the fifth mixture with slow addition of concentrated sulfuric acid to form carboxyethyl germanium sesquioxide.

3. The method of claim 2 wherein the organic solvent is a halogenated solvent.

4. The method of claim 3 wherein the solvent is selected from the group consisting of dichloromethane, carbon tetrachloride and chloroform.

5. The method of claim 4 wherein the solvent is dichloromethane.

6. The method of claim 1 wherein the non-polar alkyl solvent is hexane.

7. The method of claim 1 wherein the acidifying step is slow addition of concentrated sulfuric acid.

8. A method of preparing pure organic germanium in the absence of germanium dioxide or metallic germanium comprising;

preparing trichlorogermane propionic acid as a crude reaction product from materials not including either germanium dioxide or metallic germanium;

forming high purity crystals of trichlorogermane propionic acid from the said crude reaction product of trichlorogermane propionic acid;

forming carboxyethl germanium sesquioxide as a reaction product from hydrolysis of the trichlorogermane propionic acid.

* * * * *